United States Patent [19]

Beisel

[11] Patent Number: 4,992,045
[45] Date of Patent: Feb. 12, 1991

[54] BATTERY POWERED CONDENSER FOR ROOT CANALS

[75] Inventor: Robert F. Beisel, Robesonia, Pa.

[73] Assignee: Dentsply Research & Development Corp., Milford, Del.

[21] Appl. No.: 266,253

[22] Filed: Oct. 28, 1988

Related U.S. Application Data

[63] Continuation of Ser. No. 33,323, Apr. 1, 1987, abandoned.

[51] Int. Cl.⁵ .............................................. A61C 3/00
[52] U.S. Cl. .................................................. 433/32
[58] Field of Search ........................... 433/32, 164, 81

[56] References Cited

U.S. PATENT DOCUMENTS

| | | | |
|---|---|---|---|
| 598,303 | 2/1898 | Cruzen | 433/32 |
| 1,684,143 | 9/1928 | Pieper et al. | 219/233 |
| 1,711,539 | 5/1929 | Pieper | 219/542 |
| 1,968,867 | 8/1934 | Angell | 219/533 |
| 3,141,087 | 7/1964 | Schoenwald | 219/233 |
| 3,234,356 | 2/1966 | Babb | 128/303.1 |
| 3,526,750 | 9/1970 | Siegel | 219/233 |
| 3,614,389 | 10/1971 | Malisza | 433/32 |
| 3,698,394 | 10/1972 | Piper et al. | 128/303.1 |
| 3,886,944 | 6/1975 | Jamshidi | 128/303.1 |
| 4,074,110 | 2/1978 | Slaughter | 219/240 |
| 4,074,719 | 2/1978 | Semm | 128/303.1 |
| 4,108,181 | 8/1978 | Saliaris | 128/303.1 |
| 4,265,618 | 5/1981 | Herskovitz et al. | 433/32 |
| 4,301,357 | 11/1981 | Huffman | 219/229 |
| 4,353,698 | 10/1982 | McSpadden | 433/164 |
| 4,392,827 | 7/1983 | Martin | 433/32 |
| 4,480,996 | 11/1984 | Crovatto | 433/164 |
| 4,527,560 | 7/1985 | Masreliez | 128/303.1 |
| 4,582,488 | 4/1986 | Newman | 433/81 |

FOREIGN PATENT DOCUMENTS 192215 1/1982 Italy .
WO85/00282 1/1985 World Int. Prop. O. .

Primary Examiner—John J. Wilson
Assistant Examiner—Adriene J. Lepiane
Attorney, Agent, or Firm—Edward J. Hanson, Jr.; David E. Wheeler

[57] ABSTRACT

A self contained heated root canal dental instrument which combines the operations of a root canal spreader, a root canal condenser and a root canal filling material heater is provided. The instrument has batteries in its handle for use as a power source for heating root canal filling material and employs a non-corrosive dental tool that has a resistive element in its tip to provide the heating when electricity from the batteries is conducted through the tip. A method for making the dental tool is provided which comprises threading a resistive element through a cannula which is used as a dental tool.

20 Claims, 2 Drawing Sheets

U.S. Patent    Feb. 12, 1991    Sheet 1 of 2    4,992,045
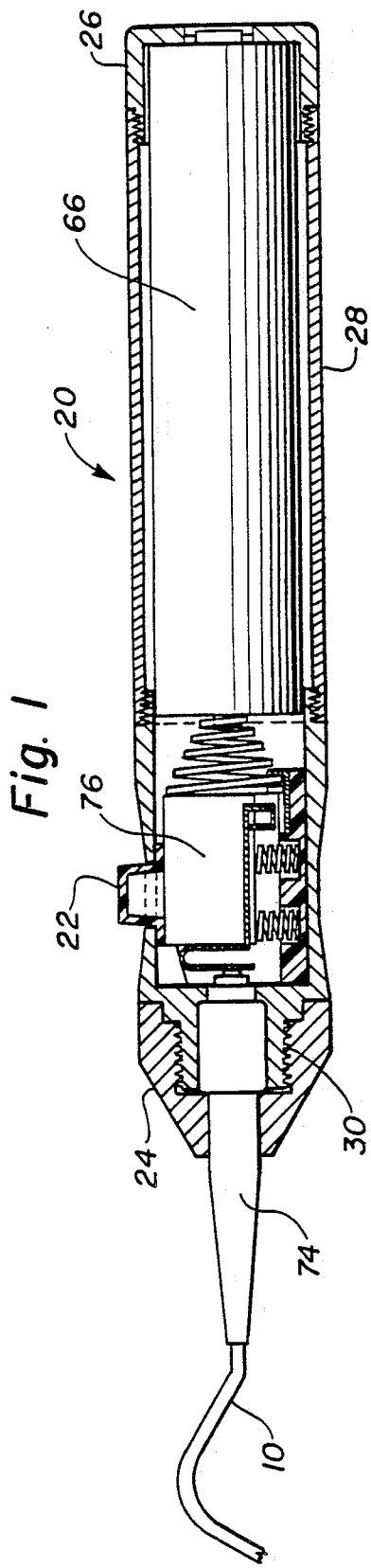
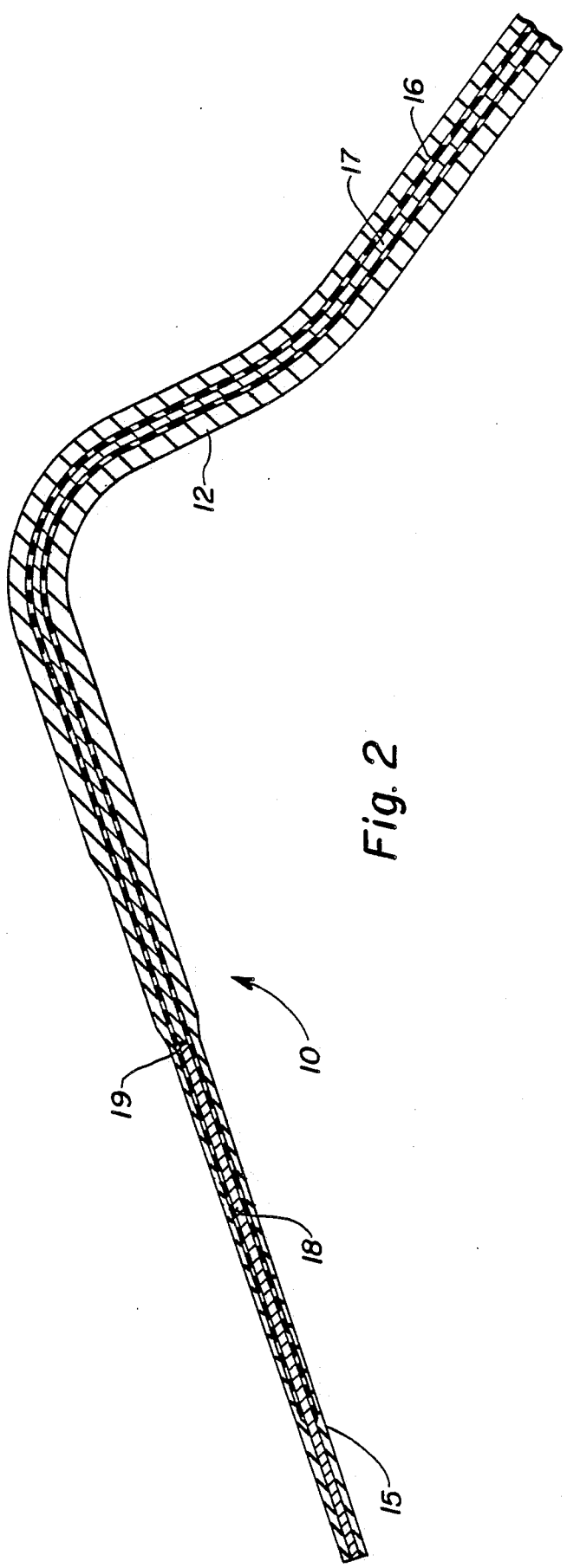

BATTERY POWERED CONDENSER FOR ROOT CANALS

This is a continuation of application Ser. No. 033,323, filed Apr. 1, 1987, now abandoned.

BACKGROUND OF THE INVENTION

1. Field of the Invention

The invention relates to a self-contained heated root canal dental instrument that combines the operations of a root canal spreader, a root canal condenser, and a root canal filling material heater.

2. Prior Art

Masreliez, in U.S. Pat. No. 4,527,560 teaches a dental probe having a resistive, integrally heated tip. The tip itself is a resistive heating element in which an electrically conductive core is surrounded by a non-conductive layer, such as dielectric insulation. The outer resistive heating layer encircles the core and is electrically connected to the core at a leading end of the core. Electrical current passing through the core and into the resistive layer causes the resistive layer to heat up. This reference, at col. 2 lines 10-14 indicates that a tip may be implemented by a resistive core surrounded by a conductive layer, but does not teach how to implement such a tip.

Martin, in U.S. Pat. No. 4,392,827 teaches a dental instrument for root canal condensation work. The tool described may be provided with a power supply component for producing heat; and a transmission component for transmitting heat produced by the power supply to a material heating component of a plugger component. The heat transmission component comprises a heating element which is folded and formed to establish a tapered section and the tapered section is covered with teflon.

3. Background

Gutta percha is the standard root canal filling material. However, it is to be understood that this invention is usable on other root canal filling materials that are spread and condensed in the root canal and which are heated to improve the flow qualities of the root canal filling material.

Gutta percha deforms when warmed and compressed. It becomes pliable at 25° to 30° Celsius, it becomes soft at 60° Celsius, and it decomposes at 100° Celsius. At such temperatures phase transitions occur allowing the gutta percha to flow into many irregularities of the prepared root canal, thus allowing for a three-dimensional obturation and sealing to occur. Such a three dimensional obturation and sealing is necessary for success in root canal therapy.

When the filling material, such as gutta percha, is softened, it is then compressed into the numerous aberrations of the root canal in order to effectively seal the root canal cavity. The compressing of the filling material in the prior art is performed by using root canal filling spreaders and filling condensers of a variety of sizes and with several handle designs (both long and short).

The filling spreaders and condensers of the prior art for root canal work are generally made of stainless steel or nickel-chromium plated brass. The filling spreaders are smooth, flat ended and slightly tapered.

The conventional means for achieving a heated instrument tip is to heat the tip externally, for example, by holding the tip in a flame or in contact with a resistive heater. The primary disadvantage of this approach is that the instrument tip cools off too rapidly, particularly if the tip is narrow. To achieve the desired degree of heating at the end of the tip, it is often necessary to heat the tip to glowing. This degree of heating increases the risk of accidental burns and tends to rapidly destroy the tip.

Heating of the tip by contact with a resistive heater sometimes involves contacting the tip between an open circuit so that current flows through the tip and thereby heats the tip. Alternatively, the instrument tip may be placed in contact with a resistive heating element so that heat is transferred to the tip by conduction. This method is similar to the common operation of a soldering iron.

A disadvantage of contacting the instrument tip across an open circuit is that sparking of the short circuit may cause "pitting" of the instrument. Also, of course, it is difficult to regulate the temperature of the tip, so the tip may be either overheated or not heated enough.

It is also known in the prior art to heat a condenser tip by providing a resistive element in said tip.

It is known in the prior art to provide an electrically heated tip in a dental instrument by using a central resistive element in a cannula in a dental instrument tip. In the prior tip, a 22 gauge cannula was crimped to one end of a NiCr element and the other end of said element was crimped in a 25 gauge cannula. Current was carried to the NiCr element by the 22 gauge cannula. A 17 gauge cannula was crimped over the 25 gauge cannula and resistive element to act as a holder for the working heated length of 25 gauge cannula. The return path for the electric current began at the very tip (crimp of 25 gauge cannula to NiCr) and continued through the outermost 17 gauge cannula. The disadvantages of this design were that the NiCr proximal to the main crimp (17 gauge to 25 gauge) was thermally isolated and reached high temperatures since it was dissipating the same high linear power densities as the exposed tip. Also, flexure of the tip had a tendency to cause a short at the crimp.

In another prior art instrument that uses a resistive element in the tip, the tip comprises a conductive core within an electrically resistive material, and heat is generated when electricity passes through the resistive material.

The concentration of heat in the prior art device relies on current density concentration from cross-sectional changes in a material of uniform volume resistivity.

Such prior art devices have the disadvantages that heat is not always generated uniformly in resistive materials and hot or cold spots may form and the large amounts of resistive material needed to cover the outer surface of the tip require relatively large amounts of electricity to provide the necessary heat. Also, electrically resistive materials are not as resistant to corrosion, and cannot be shaped as easily as stainless steel which is conventionally used for such tips.

In addition, most such devices use alternating current and must therefore be attached to cumbersome wires which provide a conduit to the power source.

Accordingly, there is a need in the art for a heat condenser having a non-corrosive tip which can be shaped using conventional means, wherein said tip uses lower amounts of electricity than conventional resistive tips, wherein said tip is made of a heat and electrically conductive material which facilitates even heating of the tip, and wherein heating of the tip can more easily be controlled.

SUMMARY OF THE INVENTION

The present invention provides a self contained heated root canal condenser instrument. The instrument comprises a hollow handle which has an aperture at one end and is open at the other end, and removable closure means are provided for the open end. A power source is provided within the hollow handle. A dental tool used for filling root canal cavities having a first end comprising a tip for working in the root canal, and a second end adapted to be attached to the hollow handle is provided. An electrically resistive element is contained within the dental tool and is attached to the dental tool at its tip. In the preferred embodiment, the power source is a battery and the dental tool is a single piece of tapered stainless steel tubing.

The dental tool used with the heated condenser is also a part of the present invention. The dental tool of the invention comprises a single piece of electrically conductive tubing and an electrically resistive element within said tubing. The resistive element makes electrical contact with the tubing at one end thereof.

The method of the invention for making the dental tool of the invention comprises silver brazing electrically conductive wire to electrically resistive wire to produce a chain wire, insulating the chain wire and threading the insulated chain wire into a single piece tubing which comprises the dental tool. In an alternative embodiment of the method, the silver brazing step may be replaced with the steps of plating an electrically resistive wire with an electrically conductive material, and stripping the electrically conductive material from the plated wire in the areas where heating is desired.

The present invention provides an easily carried (because there are no wires attached externally to the condenser) self heated condenser having a highly non-corrosive dental tool which contains a resistive element in its core. The tip of the dental tool of the invention is evenly heated, requires relatively low amounts of electricity to provide said heating, and since power to the resistive element is controlled by a switch on the instrument, heating of the dental tool can be easily controlled.

BRIEF DESCRIPTION OF THE DRAWINGS

FIG. 1 is a cutaway view of the hollow handle of the heat condenser of the invention.

FIG. 2 is a cutaway view of a dental tool of the invention.

DETAILED DESCRIPTION OF THE INVENTION

Figure 3:
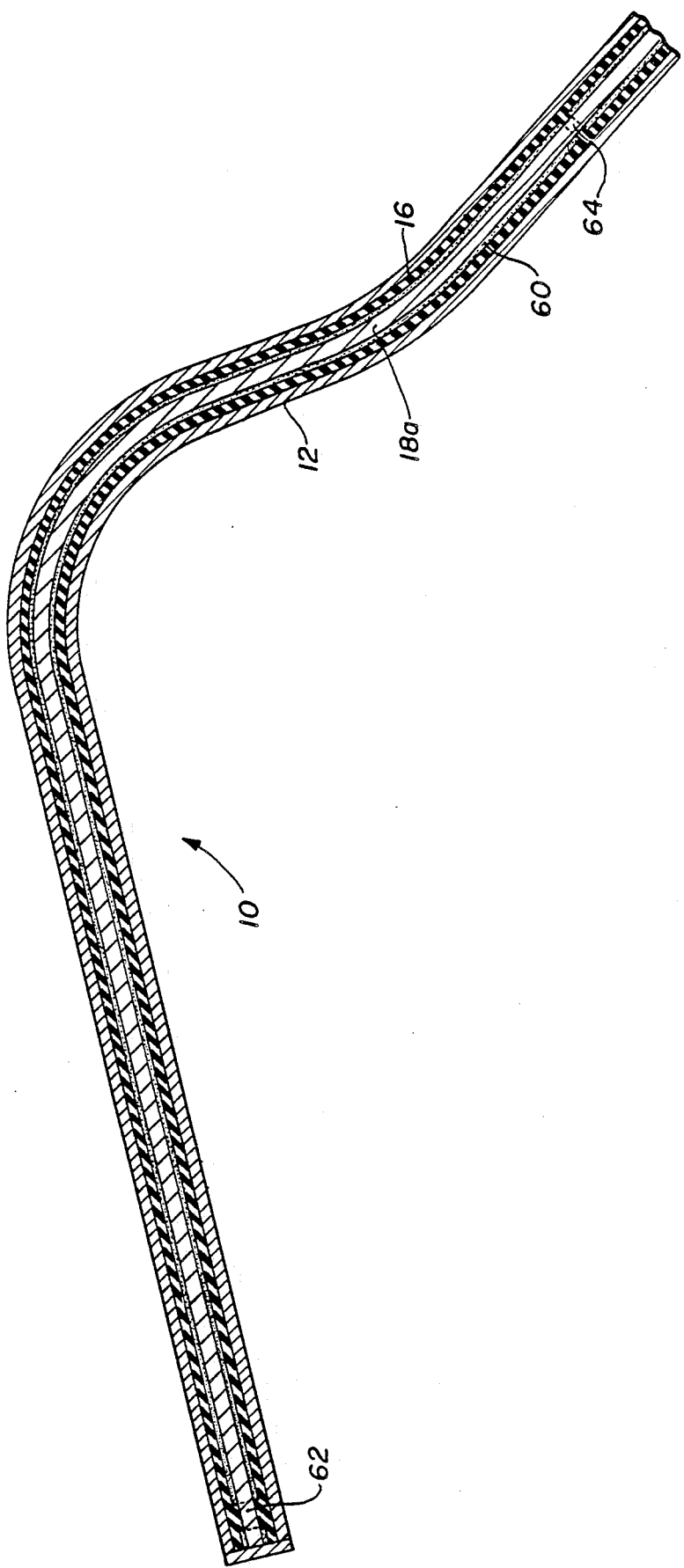
FIG. 3 is a cutaway view of an alternative embodiment of the dental tool of the invention.

With reference now to FIG. 1, the condenser 20 comprises hollow handle 28 having a removable cover 26 which is used to retain batteries 66 within the handle and also, in the preferred embodiment, has means on cover 26 through which the batteries can be recharged when the instrument is placed in a recharger. Dental tool 10 is attached to hollow handle 28 by collar 24. In the illustrated embodiment, collar 24 is an integral part of dental tool 10 and provides means for removing and attaching various sized dental tools to the aperture 30 of hollow handle 28. Aperture 30 contains conductive means for conveying electric current from the batteries 66 contained in hollow handle 28 to dental tool 10. Switch means 22 is provided for stopping and starting the flow of electric current to dental tool 10.

With reference now to FIG. 2, the dental tool 10 of the invention comprises cannula or hollow tapered tubing 12, conductor 17 contained within tapered tubing 12 which provides an electrically conductive path from hollow handle 28 to resistive element 18 in the working tip 15 of tapered tubing 12. Conductor 17 and resistive element 18 together represent the core wire. Insulator 16 separates and electrically insulates conductor 17 from tapered tubing 12.

With reference to FIG. 3, in an alternative embodiment, dental tool 10 will comprise hollow tapered tubing 12, which contains a single wire resistive element 18a which is plated with a conductive material 60, such as copper or silver, throughout its length, except in those areas 62 and 64 where it is desired that heating take place.

When dental tool 10 is attached to aperture 30 of hollow handle 28, electric current, when switch 22 is closed, travels through conductor 17 to resistive element 18 which generates the heat required for the use of the dental tool in filling a root canal. In the embodiment of FIG. 2, resistive element 18 is connected to conductor 17 through spot weld or brazed ball 19 within tapered tubing 12. To ensure that the electrical circuit travels to tip 15 of dental tool 10, to provide the required power for the heating of tip 15, insulator 16 is provided between tapered tubing 12 and conductor 17 and between tapered tubing 12 and resistive element 18 throughout dental tool 10 except for an electrical junction in tip 15. Resistive element 18 makes electrical contact with tapered tubing 12 in tip 15, and tapered tubing 12 provides a conductive return to the power source to complete an electrical circuit. The end of tubing 12 is welded to provide weld ball which is dressed to size to provide a rounded tip 15 on dental tool 10.

The handle 28 of the condenser of the invention, in the illustrated embodiment, uses battery 66 as a power source. Bottom cap assembly 26 is used to close the end of handle 28 and enclose battery 66. Enlarged end 74 of dental tool 10 is retained on handle 28 by collar 24. Enlarged end 74 and collar 24 act as a heat sink for dissipating heat when the dental instrument is used. In the illustrated embodiment, the current in the instrument is controlled by microswitch 76 which is activated by switch means 22.

It has been found that in the dental tool of the invention, heat sufficient to plasticize gutta percha is produced using only a 2.5 volt D.C. source (two standard AA batteries) using only about 3 ohm resistance in tip 15, about 0.1 ohm of which is due to the resistance of tapered tubing 12. Although tubing 12 may be more resistive to electrical conductivity than copper or silver, for example, it is preferred that the material of tapered tubing 12 be substantially more conductive than resistive element 18. It has been found that two AA batteries generally produce enough power that, if the switch is closed for a substantial period of time, the tip will overheat, and to avoid this problem, a small resistor is included in tapered tubing 12, near collar 24, to dissipate a fraction of the power before it reaches tip 15. In other embodiments, it is believed that two AAA batteries may be used. The enlarged end 74 and collar 24 dissipate the heat generated by the small resistor. In the alternative embodiment of FIG. 3 an area 64 may be provided if needed to dissipate any excess heat generation capacity and thereby refine the exact amount of heat capacity available in area 62.

In an alternative embodiment, handle 28 may contain a transformer or other similar means for providing a source of power for heating dental tool 10.

The heat generation along tip 15 is generally uniform due generally to the heat conductivity and the single piece construction of the material used to make tubing 12. Heat dissipates from the dental tool 10 very quickly when switch 22 is open because of the mass of conductive material in the wider areas of tapered tubing 12 and the collar 24, and this reduces the chances that the practitioner will cause inadvertent burns in the mouth since it is possible to insert the dental tool into the root canal, close the switch to cause heating of the filling material, open the switch and let the heat dissipate, and never have a heated dental tool anywhere in the mouth except in the root canal.

Tapered tubing 12 will preferably be made of an electrically conductive, non-corrosive material. In the illustrated embodiment tapered tubing 12 will be a single piece of work hardened austenitic stainless steel tubing which has a diameter of about 0.030 inch and said steel tubing is ground to provide a taper of about 0.020 inch per inch in the tip region to provide a tip having a diameter of about 0.012 to 0.016 inch. In the embodiment of FIG. 2, the NiCr wire core which preferably comprises resistive element 18 will be about 0.005 inch in diameter and will have a length of about $\frac{3}{8}$ inch. In the most preferred embodiment, the resistive element 18 will be a special type of NiCr known as Stablohm-800 which has about 30% greater resistivity than standard NiCr wire. The conductive core will preferably be 0.005 inch diameter copper wire. The insulation can be any heat resistive (heat generated by the tip reaches a maximum of about 250° C.) organic material that is an insulator against electricity and preferably will be 0.0025 inch thick polyimide.

In the embodiment of FIG. 3, which is considered preferred, resistive element 18a will have a diameter of about 0.005 inch and will traverse the full length of the dental tool 10, and will be plated with conductive material throughout its length, except where it is desired that heating take place. In such an embodiment the conductive plating on the outside of the resistive element will carry almost all of the electrical current since the conductivity of the plating material is much greater than the conductivity of the resistive wire. The resistive element, therefore, will provide negligible heating in the areas where plating is retained, but will heat normally where the plating is removed, and current is forced to pass through the resistive material. Accordingly, in the embodiment of FIG. 3, the added expense of providing and brazing two resistive elements in the dental tool 10 will be avoided since the plated resistive wire can be mass produced and the conductive material plating can be chemically or abrasively stripped in the areas where it is desired that heating take place. The chemicals that may be used for chemically stripping the conductive material are well known to those skilled in the art.

The stripping process is less labor intensive than the brazing process, and accordingly, it is easier and less expensive to provide a resistive element in a dental tool using the stripping method as compared to the brazing method. In addition, since the brazing method produces a weld or ball that has a tendency to be larger than the diameter of the core wire, the brazed ball has a tendency to cause frictional binding and to abrade in the manufacturing process, and this problem is avoided using a single strand of plated resistive wire.

In the method of manufacturing the embodiment of FIG. 2, strands of conductive wire are brazed or spot welded to strands of resistive wire to produce a chain wire which is dipped into the polymer used for insulation, and the polymer is cured. The insulation is stripped at the ends where electrical contact is desired and the insulated wire is threaded through the cannula. The wire is then cut to the desired length and the end in the tip of the cannula is welded and the weld ball formed is dressed to size to provide a smooth rounded tip. The cannula is then bent to shape.

In the method of manufacturing the embodiment of FIG. 3, a single strand of resistive wire is plated with a conductive material, such as silver or copper, by directing the resistive wire through a plating means such as an electroplating bath. The plating is stripped from the resistive wire chemically or abrasively in those areas where it is desired that heating take place in the resistive wire and the resistive wire is then covered with insulating material as described above. The dental tool of the invention is then assembled as described above.

Although a tapered dental tool is shown in the illustrated embodiment, and is most convenient, those skilled in the art will recognize that a dental tool with a uniform diameter of about 0.01 to 0.025 inch may be used.

In the illustrated embodiment, switch 22 provides only for opening and closing the electrical circuit. Those skilled in the art will recognize that a variable resistor may be provided in series with switch 22 which may be used to control the heating of tip 15 by reducing the total current that reaches resistive element 18.

The dental tool 10 may be fastened to hollow handle 20 at any of four positions relative to switch 22 at 90° intervals, one position being aligned with switch 22. This makes it possible for the practitioner to attach the dental tool in a position that is convenient for working on a particular root canal.

The dental tool of the invention may be provided with a gooseneck shape to provide easy access in the mouth and at least two tip designs may be provided; an anterior tip for working on forward teeth is longer than a posterior tip and is provided with an obtuse angle; the angle of a posterior tip is more near 90° and is suitable for working on back teeth.

While present embodiments of the invention have been illustrated and described, it will be recognized by those skilled in the art that this invention may be otherwise variously embodied and practiced within the scope of the following claims.

It is claimed:
1. A self-contained heated dental instrument comprising:
   (a) a dental tool means for filling root canal cavities comprising a single piece of electrically conductive tubing, said dental tool means having a first end comprising a tip for working in the root canal, and a second end adapted to be attached to a handle means, said dental tool means being shaped to be adapted for use in the mouth,
   (b) an element within said dental tool means comprising a conductive portion and a resistive portion, said resistive portion being conductively connected to the tip of said dental tool, wherein said element is provided with insulating substantially throughout its length, (c) a resistor in said conductive portion of said element substantially proximal to said second end of said dental tool, said resistor being provided to control the heating of said first end of said heated tool, (d) handle means having an aperture at one end for receiving said dental tool and (e) a power source means associated with said handle means.

2. The self-contained heated dental instrument of claim 1 in which said resistive element comprises a NiCr wire which is attached to a copper wire through a brazed ball within said dental tool wherein said NiCr wire is about ½ to ⅛ the length of said dental tool.

3. The self-contained heated dental instrument of claim 2 in which said NiCr wire comprises about 1/5 of the length of said dental tool.

4. The self-contained heated dental instrument of claim 1 in which said element is plated with electrically conductive material throughout its length except where heating of the element is desired.

5. The self-contained heated dental instrument of claim 1 in which said power source is battery means.

6. The self-contained heated dental instrument of claim 5 in which said power source is rechargeable.

7. The self-contained heated dental instrument of claim 1 in which said tubing is stainless steel.

8. The self-contained heated dental instrument of claim 1 in which said aperture is adapted for removal and attachment of said dental tool.

9. The self-contained heated dental instrument of claim 1 in which said insulation comprises polyimide.

10. The self-contained heated dental instrument of claim 1 in which said element is attached to said tip of said dental tool by weld means.

11. A dental tool for heating filling material in a root canal comprising:

(a) a single piece of electrically conductive tubing, having a first end comprising a tip for working in a root canal, and (b) an element within said tubing comprising a conductive portion and a resistive portion wherein said element is insulated from said tubing substantially throughout its length, said element having electrical contact with said tubing substantially at said tip, and wherein a resistor is provided in said conductive portion proximal to a second end of said dental tool for controlling the heating of said first end of said dental tool.

12. The dental tool of claim 11 in which said element is attached to said tubing by weld means at one end thereof.

13. The dental tool of claim 11 in which said element comprises NiCr wire which is attached to a conductor within said tubing.

14. The dental tool of claim 13 in which said NiCr wire is about ½ to ⅛ the length of said tubing.

15. The dental tool of claim 13 in which said NiCr wire is about 1/5 the length of said dental tool.

16. The dental tool of claim 11 in which said element comprises electrically resistive wire plated with an electrically conductive material throughout its length except where heating is desired.

17. A self-contained heated dental instrument comprising:

(a) a dental tool means for high temperature treatment in the mouth comprising a single piece of electrically conductive tubing, said dental tool means having a first end for working in the mouth, and a second end adapted to be attached to a handle means, said dental tool means being shaped to be adapted for use in the mouth, (b) a wire element within said dental tool means comprising a conductive portion and a resistive portion, said resistive portion being conductively connected to said first end of said dental tool, wherein said wire element is insulated from said dental tool substantially throughout its length, (c) a resistor in said conductive portion of said element substantially proximal to said second end of said dental tool, said resistor being provided to control the heating of said first end of said dental tool, (d) handle means having an aperture at one end for receiving said second end of said dental tool and (e) a power source means associated with said handle means.

18. The self-contained heated dental instrument of claim 17 in which said wire element comprising NiCr wire which comprises about 1/5 of the length of said dental tool.

19. The self-contained heated dental instrument of claim 17 in which said element is a resistive element which is plated with an electrically conductive material throughout its length except where heating of the element is desired.

20. The self-contained heated dental instrument of claim 17 in which said dental tool is tapered to facilitate heating of the walls of a root canal cavity.

* * * * *